US009095160B2

(12) United States Patent
Beasley et al.

(10) Patent No.: US 9,095,160 B2
(45) Date of Patent: Aug. 4, 2015

(54) PROBIOTIC PREPARATION FOR THE PREVENTION OR TREATMENT OF CANINE GASTROINTESTINAL DISORDERS

(75) Inventors: Shea Beasley, Helsinki (FI); Kalevi Heinonen, Hautjarvi (FI); Hanna Lehmussola, Piispanristi (FI)

(73) Assignee: VETCARE OY, Muurla (FI)

( * ) Notice: Subject to any disclaimer, the term of this patent is extended or adjusted under 35 U.S.C. 154(b) by 633 days.

(21) Appl. No.: 13/389,948

(22) PCT Filed: Jun. 23, 2010

(86) PCT No.: PCT/FI2010/050538
§ 371 (c)(1),
(2), (4) Date: Apr. 25, 2012

(87) PCT Pub. No.: WO2011/018547
PCT Pub. Date: Feb. 17, 2011

(65) Prior Publication Data
US 2012/0201796 A1    Aug. 9, 2012

(30) Foreign Application Priority Data
Aug. 12, 2009    (FI) ..................... 20095836

(51) Int. Cl.
| A01N 63/00 | (2006.01) |
| C12N 1/20 | (2006.01) |
| A23K 1/18 | (2006.01) |
| A23K 1/00 | (2006.01) |
| A23K 1/175 | (2006.01) |
| A61K 35/74 | (2015.01) |

(52) U.S. Cl.
CPC ............... *A23K 1/1846* (2013.01); *A23K 1/009* (2013.01); *A23K 1/1753* (2013.01); *A61K 35/74* (2013.01)

(58) Field of Classification Search
None
See application file for complete search history.

(56) References Cited

U.S. PATENT DOCUMENTS

| 4,806,368 A | 2/1989 | Reddy |
| 5,876,990 A * | 3/1999 | Reddy et al. .................. 435/177 |
| 6,132,778 A | 10/2000 | Kasler et al. |
| 2005/0158293 A1 | 7/2005 | Boileau et al. |
| 2005/1017559 | 8/2005 | Boileau et al. |
| 2007/0009502 A1 | 1/2007 | Lall et al. |

FOREIGN PATENT DOCUMENTS

| EP | 0 287 699 A2 | 4/1987 |
| EP | 0850569 A1 | 7/1998 |
| EP | 1290136 A1 | 3/2003 |
| WO | WO-0054788 A1 | 9/2000 |
| WO | WO-0117366 A1 | 3/2001 |
| WO | WO-04/000340 A2 | 12/2003 |
| WO | WO-2005/060707 A2 | 7/2005 |
| WO | WO-2006/110407 A1 | 10/2006 |
| WO | WO-2007/076534 A1 | 7/2007 |
| WO | WO-2007/126990 A2 | 11/2007 |
| WO | WO 2009/021824 A1 | 2/2009 |

OTHER PUBLICATIONS

Beasley S.S. et al., "Lactic acid bacteria isolated from canine faeces", Journal of Applied Microbiology, vol. 101, pp. 131-138, 2006.
McCoy S. et al., "Isolation and characterization of *Lactobacillus* species having potential for use as probiotic cultures for dogs", Journal of Food Science, vol. 72, No. 3, pp. M94-M97, 2007.
Manninen T. et al., "Alteration of the Canine Small-Intestinal Lactic Acid Bacterium Microbiota by Feeding of Potential Probiotics," Applied and Environmental Microbiology, vol. 72, No. 10, pp. 6539-6543, 2006.
Search Report from priority application FI20095836, 2010.
Scholz-Ahrens et al., "Prebiotics, Probiotics, and Synbiotics Affect Mineral Absorption, Bone Mineral Content, and Bone Structure," J. Nutr. (2007), vol. 137, pp. 838S-846S.
Supplementary European Search Report issued Apr. 7, 2015, in European Patent Application No. 10 80 8015.

* cited by examiner

*Primary Examiner* — Chris R Tate
*Assistant Examiner* — Douglas F White
(74) *Attorney, Agent, or Firm* — Birch, Stewart, Kolasch & Birch, LLP

(57) ABSTRACT

The present invention relates to a probiotic preparation for preventing and treating canine gastrointestinal disorders containing at least two dog-specific strains of lactic acid bacteria belonging to genus *Lactobacillus*, a calcium source in an amount of 20-99 weight-% expressed as $CaCO_3$ of the dry weight of the preparation, and at least one prebiotic, and optionally additional dog-specific strains of lactic acid bacteria, excipients and carriers. The invention further relates to a process for the manufacture of the probiotic preparation, to dog food comprising the probiotic preparation, and to the use of the probiotic preparation for the manufacture of a pharmaceutical product or a dog food product for preventing and treating canine gastrointestinal disorders.

14 Claims, No Drawings

PROBIOTIC PREPARATION FOR THE PREVENTION OR TREATMENT OF CANINE GASTROINTESTINAL DISORDERS

This application is the National Phase Under 35 U.S,C. § 371 of PCT International Application No. PCT/FI2010/050538 which has an International filing date of Jun. 23, 2010, which claims priority to Finnish Application No. 20095836 filed on Aug. 12, 2009. The entire contents of all applications listed above are hereby incorporated by reference.

FIELD OF THE INVENTION

The present invention relates to a probiotic preparation for preventing or treating gastrointestinal disorders in dogs. The invention further relates to a process for the manufacture of the probiotic preparation, to dog food comprising the probiotic preparation and to use of the probiotic preparation for the manufacture of pharmaceuticals or dog food products.

BACKGROUND OF THE INVENTION

Continuous or intermittent diarrhoea is very common among dogs. When the symptoms are mild, the owner may try to alleviate the diarrhoea by fasting, changing diet, feeding fermented dairy products and medicinal products available without prescription. If the condition of the dog weakens, the animal is taken to a vet for examination and laboratory experiments. The diarrhoea may be derived from small intestines, from large intestines or it may involve both intestines. The diagnosis is made based on the symptoms, appearance of faeces, anamnesis, physical examination and laboratory tests.

The spectrum of canine gastrointestinal disorders involving chronic diarrhoea is wide: protein-losing enteropathy; lymphangiectasis; foodborne diarrhoea; inflammatory bowel disease including lymphocytic-plasmacytic gastroenteritis, eosinophilic gastroenterocolitis, regional granulomatous enteritis, histiocytic ulcerative colitis, and suppurative enterocolitis; irritable bowel syndrome; villus atrophy; diarrhoea caused by intestinal parasites and protozoan; bacterial and viral infections; antibiotic responsive diarrhoea (small intestinal bacterial overgrowth). Also other causatives of diarrhoea have been identified such as opportunistic fungi and algae, intestinal tumours and blockage, as well as some non-gastrointestinal disorders such as renal insufficiency, disorders of liver, right cardiac insufficiency, adrenal insufficiency, and diabetes mellitus. Also stress can trigger diarrhoea by reducing secretion of gastric hydrochloric acid, or by altering the population or activity of the intestinal flora. In many cases the aetiology remains unknown, and the diarrhoea is treated symptomatically.

The traditional approach to the treatment of canine gastrointestinal problems relies on dietary modifications, antibiotic treatment, and specific anti-inflammatory and immunosuppressive drugs, either individually or combined. Many of the canine gastrointestinal disorders are treated with antibiotics, even when the diagnosis is uncertain or yet tentative. This treatment may involve even weeks of antibiotic therapy with several renewals. Due to increasing problems with antimicrobial resistance, alternative therapies should be considered. As one of the alternative therapies treatment with probiotic bacteria, especially with lactic acid bacteria, have been suggested due to their health-conferring properties.

Lactic acid bacteria form a heterogenous group of gram-positive bacteria. The bacteria included in the group are non-sporing, nonrespiring cocci or rod, which produce lactic acid as the major end product during the fermentation of carbohydrates. The best-known genera are *Enterococcus, Lactobacillus, Lactococcus, Leuconostoc, Pediococcus, Streptococcus* and *Weissella, Lactobacillus* being the largest genus consisting of about 80 recognized species. Lactic acid bacteria constitute an important part of the human and animal intestinal microbiota. Although lactic acid bacteria are known to play an important role in the intestine in protecting the host against pathogenic species, only little is known on the role of these bacterial species in canine intestine. Most of the recognized canine intestinal lactic acid bacteria belong to the genera *Streptococcus* and *Lactobacillus*.

Probiotics are living microbes, microbial cell preparations or components of microbial cells that are used to promote health as such or as a food product. These microbes usually belong to the species *Lactobacillus* sp. or *Bifidobacterium* sp. The ingestion of probiotic lactic acid bacteria has many documented or potential benefits, such as modulation of the GI-tract, antagonism against pathogenic microbes, and maintaining the intestinal mucosal barrier. Adhesion to the intestinal mucosa is considered to be one of the main mechanisms for the probiotic lactic acid bacteria to benefit the health of the host. Probiotic lactic acid bacteria have been proposed to function through several mechanisms to exert their beneficial biological effects on the host: Competing for nutrients and epithelial attachment sites prevents colonization of the host. Probiotics produce antimicrobial compounds and acids reducing intestinal pH making the environment for undesirable microbes, such as pathogens, unfavorable. In addition, probiotic lactic acid bacteria recruit immune cells and activate immune and/or inflammatory responses by altering cytokinone and chemokine release as well as secret antimicrobial peptides. The ability of probiotic bacteria ingestion to alter the nasal and vaginal microbiota suggests that intestinal microbiota activates immune responses located to mucosa-associated lymphoid tissues. Probiotic administration has been associated with decreased risk of systemic conditions such as allergy and infection of ear, urinary tract and vagina.

Some strains of lactic acid bacteria have been documented to have beneficial effects on the health of dogs. In order to be successful probiotics, bacteria should survive the gastrointestinal tract and therefore tolerate bile and the acid conditions of the gut. The probiotic characteristics of bacteria are also linked to host specificity, which is a very important criterion for selection of a probiotic. Host specificity is required by law in human probiotics. Most of the commercial probiotic strains aimed for dogs are not from canine origin. Furthermore, majority of the probiotic preparations for animals contain *Enterococcus faecium*, which has been shown to have negative effects due to its potential pathogenic characteristics.

Beasley S. et al, (Lactic acid bacteria isolated from canine faeces, Journal of Applied Microbiology, 101 (2006) 131-138) disclose the isolation and sequencing of lactic acid bacteria from the faeces of healthy dogs. Five of the strains, *Lactobacillus fermentum, L. mucosae, L. rhamnosus, L. salivarius* and *Weissella confusa*, were selected as candidate probiotics based on their frequency, quantity in faeces, growth density, acid tolerance and anti-microbial activity.

The research of Beasley et al was continued by Manninen T. et al. (Alteration of the Canine Small-Intestinal Lactic Acid Bacterium Microbiota by Feeding of Potential Probiotics, Applied and Environmental Microbiology, Oct. 2006, p. 6539-6543) in an examination of the in vitro tolerances of the above-mentioned five candidate probiotic strains of lactic acid bacteria to canine jejunal chyme. The strains were fed twice a day mixed with dog food for 7 days to five permanently fistulated beagles. The strains were found to survive in and to dominate the jejunal chyme lactic acid microbiota during feeding and to have the ability to modify the intestinal microbiota.

In addition to use of probiotics, also other approaches to modify canine gut flora have been disclosed. Oligosaccharides such as inulin and various fructo-oligosaccharides have been reported to favour the growth of bifidobacteria and lactobacteria in the gastro-intestinal tract and to decrease the amount of pathogens such as Clostridium perfringens. EP 0 850 569 B1 discloses a cereal product useful as a pet food comprising a gelatinized starch matrix containing prebiotic oligosaccharide in the form of inulin, and optionally also prebiotic fructo-oligosaccharide. This product is said to have beneficial effect in the gastro-intestinal tract of the consumer and hence upon the consumer as a whole. When fed to dogs improved palatability, increased bifidobacteria counts, decreased C. perfringens counts, and decreased faecal pH, odour and volume were reported.

Also probiotics combined with other potentially beneficial substances have been disclosed. WO 2007/076534 discloses a composition comprising at least one antioxidant such as vitamin E, vitamin C and/or β-carotene optionally in conjunction with one or more of a probiotic and a prebiotic. As suitable probiotics several species of Bifidobacterium and Lactobacillus are listed, oligosaccharides, galactans and β-glucans being mentioned as suitable prebiotics. The composition is stated to be useful for enhancing the balance of beneficial and deleterious bacteria in the gastrointestinal tract of an animal having a risk for inflammatory bowel disease, said animals including humans as well as avian, bovine, canine, equine, feline, hircine, murine, ovine and porcine animals.

US 2005/0175598 A1 discloses methods of use of probiotic Bifidobacteria, obtainable by isolation from resected and washed GI tract of mammals, preferably of dogs, in companion animals, these methods including treatment of immune system, weight control and body composition, urinary health, skin and coat diseases, and ageing. Said probiotics can be administered orally in viable or non-viable form, for example prepared into a composition for normal dietary intake such as kibbles and wet animal food, or to be used as a supplement, exemplified by biscuits, chews, treats, powders, suspensions, and capsules. As additional components the compositions may comprise protein, fat, carbohydrate, prebiotics, long-chain fatty acids, and zinc. Examples of prebiotics include oligosaccharides, fructo-oligosaccharides, galacto-oligosaccharides, xylo-oligosaccharides, and oligo derivatives of starch.

EP 1 290 136 B1 discloses six novel probiotic strains of lactic acid bacteria: feline Lactobacillus reuteri NCC2581, Lactobacillus reuteri NCC2592 and Lactobacillus rhamnosus NCC2583, and canine Lactobacillus reuteri NCC2603, Lactobacillus reuteri NCC2613 and Lactobacillus acidophilus NCC2628. Also disclosed is a method of obtaining probiotic strains for cats and dogs, including isolating lactic acid bacteria strains from cats and dogs faeces, and selecting strains having the capability to grow producing at least 1.0E+06 cfu/ml in the presence of up to 2.0% bile salts, and having the capability to grow producing at least 1.0E+06 cfu/ml after 2 hours at a pH range from 3.4 to 4.2. Also disclosed is a method of preparing a dog or cat food composition including an additional step of incorporating the selected strain(s) into a dog or cat food composition. As suitable bacterial strains Lactobacillus reuteri, L. acidophilus, L. animalis, L. ruminis, L. johnsonii, L. casei, L. paracasei, L. rhamnosus, L. fermentum, Bifidobacterium sp., Enterococcus faecium, and Enterococcus sp. are listed. The pet food is intended for the health of the gastrointestinal tract and skin and/or coat system of cats and/or dogs, and ameliorating or reducing the effects of ageing. The pet food may contain, in addition to the bacteria strains and/or its fermented medium, a starch source, a protein source and lipid source, a prebiotic carbohydrate in an amount of less than about 20 % by weight of the dried pet food, as well as long chain fatty acids, minerals and vitamins to supplement the pet food into a nutritionally complete product.

Despite of the variety of the state of the art solutions and recent developments in the field, it is clear that there still is a need for a dog-specific preparation, which can be used for preventing and treating a wide spectrum of canine gastrointestinal disorders, and secondary conditions originating from these disorders, preferably avoiding the use of antibiotics. The benefits of the present preparation are seen especially in chronic disorders requiring long-term treatment, and in disorders not responding to other therapies or to specific diet.

OBJECT OF THE INVENTION

An object of the present invention is to provide a probiotic preparation for preventing and treating canine gastrointestinal disorders.

Another object of the present invention is to provide a dog food product containing the probiotic preparation for preventing and treating canine gastrointestinal disorders and maintaining the health when improving the natural immunosuppressive status of the dog.

Yet another object of the invention is a process for the manufacture of the probiotic preparation.

An additional object of the present invention is the use of the constituents of the probiotic preparation for the manufacture of a pharmaceutical or a dog food product for preventing and treating canine gastrointestinal disorders.

The characteristic features of the probiotic preparation, the dog food product, the process for the manufacture, and the use of the constituents of the probiotic preparation for the manufacture of a dog food or a pharmaceutical composition are disclosed in the claims

SUMMARY OF THE INVENTION

The invention is directed to a probiotic preparation for preventing and treating canine gastrointestinal disorders, and secondary conditions originating therefrom, said preparation comprising dog-specific strains of lactic acid bacteria, at least two of the strains belonging to genus Lactobacillus, at least one prebiotic, and a high calcium content.

The invention is also directed to a process for the manufacture of a probiotic preparation. The process involves culturing either separately or together dog-specific strains of lactic acid bacteria, at least two of the strains belonging to genus Lactobacillus, and processing the obtained culture(s), at least one prebiotic, and a calcium source present in an amount of 20-99 weight-%, expressed as $CaCO_3$ of the dry weight of the final preparation, and optionally additional dog-specific strains of lactic acid bacteria, conventional excipients and carriers, into a homogenous preparation.

The probiotic preparation of the invention can be used for the prevention and treatment of canine gastrointestinal disorders either as dry powder, mixed into a dog food or formulated into more specific pharmaceutical formulations or dog food products e.g. for oral administration, such as into granules, tablets, chewing snacks and fermented products.

In the following, the invention is illustrated by detailed description, and by examples without wishing to limit the invention thereto.

DETAILED DESCRIPTION OF THE INVENTION

It has now been found that a probiotic preparation comprising a specific combination of at least two dog-specific strains of lactic acid bacteria belonging to genus *Lactobacillus*, a calcium source in an amount of 20-99 weight-% expressed as $CaCO_3$ of the dry weight of the preparation, and at least one prebiotic, exerts beneficial effect to dogs suffering from a wide spectrum of gastrointestinal disorders of both known and unknown aetiology, and from secondary conditions deriving from these disorders. Optionally the probiotic preparation of the invention may further comprise additional dog-specific strains of lactic acid bacteria, conventional excipients and carriers.

The amount of each dog-specific strain of lactic acid bacteria may range between a minimum amount needed for a probiotic effect, i.e. $1*10^6$ cfu/g, and $1*10^{13}$ cfu/g. In a more favourable preparation in view of the probiotic effect and economical aspects, the amount of each dog-specific strain of lactic acid bacteria ranges from $1*10^7$ to $1*10^{10}$ cfu/g, preferably from $5*10^8$ to $2.5*10^9$ cfu/g of the probiotic preparation. This concentration builds a sufficient amount of said strains to the GI tract to act beneficially. The dog-specific strains of lactic acid bacteria may be incorporated into the probiotic preparation of the invention as lyophilised cultures thus bringing residues of fermentation medium to the preparation. These residues act as protective agents to the probiotics, and as initial growth material to the bacteria in the GI tract after digestion, either as such or pre-fermented by other microbes in the gut. These residues typically comprise up to 15 weight-% of the dry weight of the probiotic preparation, preferably up to 5 weight-% of the dry weight of the probiotic preparation.

Herein by the expression of "dog-specific strains of lactic acid bacteria" it is meant lactic acid producing bacteria isolated from canine faeces, canine intestines or intestinal fluids. The bacteria strains are selected on the basis of their dominant growth in canine intestine, ability to survive in the GI tract, perform antimicrobial activity and tolerate anaerobical and aerobical atmosphere. Advantageously at least one of the selected strains is resistant to antibiotics.

The "dog-specific strains of lactic acid bacteria"may be obtained by isolating different "dog-specific strains of lactic acid bacteria"from the faeces of healthy dogs, and selecting from the isolated strains at least two strains belonging to genus *Lactobacillus*. The isolation of the "dog-specific strains of lactic acid bacteria"from the faeces of healthy dogs may be performed as disclosed by Beasley et al. (Lactic acid bacteria isolated from canine faeces, Journal of Applied Microbiology, 101 (2006) 131-138). The selection criteria may include capability to grow in low pH (in pH 1-2), tolerance to bile acid and oxygen, resistance to some specific antibiotics such as amoxicillin, erythromycin, chloramphenicol, ampicillin, ciprofloxacin, enrofloxacin, gentamicin, kanamycin, quinupristin/dalfopristin, streptomycin, vancomycin, tetracycline, trimethoprim, rifampin, linezolid, cephalosporins, and klindamycin, or antimicrobial activities towards some specific pathogens such as *Micrococcus luteus*, or certain species of *Enterococcus* and *Clostridia* recognised as opportunistic pathogens. Preferably, the chosen bacteria are not affected by protease treatment indicating either protease resistance or a non-protein nature of the antimicrobial substance.

Possible "dog-specific strains of lactic acid bacteria"belonging to genus *Lactobacillus* that may be used in the probiotic preparation of the invention include strains of, without any limitation, *L. acetotolerans, L. acidophilus, L. agilis, L. alimentarius, L. animalis, L. bifermentans, L. brevis, L. buchneri, L. Casei, L. crispatus, L. crustorum, L. curvatus, L. delbrueckii, L. fermentum, L. Gallinarum, L. gasseri, L. gastricus, L. helveticus, L. intestinalis, L. jensenii, L. Johnsonii, L. kefiri, L. leichmannii, L. mucosae, L. murinus, L. oligofermentans, L. parabuchneri, L. parakefiri, L. paraplantarum, L. pentosus, L. plantarum, L. Rennini, L. reuteri, L. rhamnosus, L. rogosae, L. salivarius, L. sharpeae, L. Ultunensis, L. vaccinostercus, L. vaginalis, L. zeae,* and *L. zymae.*

Preferably in the probiotic preparation of the invention at least one of the dog-specific strains of lactic acid bacteria belonging to genus *Lactobacillus* is selected from *Lactobacillus fermentum, Lactobacillus plantarum, Lactobacillus rhamnosus, Lactobacillus salivarius,* and *Lactobacillus Mucosae*. More preferably, said dog-specific strains of lactic acid bacteria belonging to genus *Lactobacillus* comprise two to five strains selected from *Lactobacillus fermentum, Lactobacillus plantarum, Lactobacillus rhamnosus, Lactobacillus salivarius, Lactobacillus casei, Lactobacillus paraplantarum, Lactobacillus pentosus, Lactobacillus reuterii, Lactobacillus murinus* and *Lactobacillus mucosae*. All these bacteria have a long washout period, they can be isolated from canine jejuni via a fistula for three weeks after last feeding. One particularly preferable embodiment contains *Lactobacillus fermentum* NCIMB 41636 and *Lactobacillus plantarum* NCIMB 41638 as the dog-specific strains of lactic acid bacteria belonging to genus *Lactobacillus*. Another preferable embodiment contains *Lactobacillus fermentum* NCIMB 41636, *Lactobacillus plantarum* NCIMB 41638 and *Lactobacillus rhamnosus* NCIMB 41640 as the dog-specific strains of lactic acid bacteria belonging to genus *Lactobacillus*. These strains were deposited on 30 Jun. 2009 in the National Collections of Industrial, Food and Marine Bacteria (NCIMB), Ferguson Building, Craibstone Estate, Bucksburn, Aberden AB21 9 YA.

Optionally the preparation may comprise additional dog-specific strains of lactic acid bacteria, other than those belonging to genus *Lactobacillus*, for example strains belonging to genus *Pediococcus*, such as *P. acidolactici*, or to genus *Weissella*, such as *W. confusa* and *W. cibaria*. Examples of preferable additional dog-specific strains of lactic acid bacteria other than *Lactobacillus*, are *P. acidolactici* NCIMB 41637 and *W. confusa* NCIMB 41639. These strains were deposited on 30 Jun. 2009 in the National Collections of Industrial, Food and Marine Bacteria (NCIMB), Ferguson Building, Craibstone Estate, Bucksburn, Aberden AB21 9YA.

The calcium source may be any calcium-containing substance acceptable for use in oral formulations for dogs. Non-limiting examples of calcium source useful in the invention are calcium carbonate, calcium ascorbate, calcium alginate, calcium stearoyl-2-lactylate, calcium sorbate, calcium formiate, calcium acetate, calcium propionate, calcium lactate, calcium citrate, calcium stearates, synthetic calcium silicate, calcium tetrahydrogen-diorthophosphate, calcium hydrogen ortho-phosphate, calcium hydroxide, calcium oxide, dicalcium diphosphate, calcium gluconate, calcium sulphite, calcium hydrogensulphite, calcium aluminium silicate, calcium digluconate, calcium guanylate, calcium inosinate, calcium-5'-ribonucleotides, calcium malate, calcium tartrate, calcium dinatrium EDTA, mono and dicalcium diphosphate, (sodium) calcium polyphosphate, calcium chloride, calcium ferrocyanide, calcium orthophosphate, and combinations thereof.

Preferably the calcium source is calcium carbonate due to its well-accepted nature and its absorpability. In addition, calcium carbonate is cost effective compared to equivalent calcium sources. Calcium absorption improves in the presence of prebiotics increasing whole body mineral content. The amount of the calcium source ranges from 20 to 99 weight-%, preferably from 40 to 95 weight-%, and even more preferably from 60 to 90 weight-% expressed as $CaCO_3$ of the dry weight of the preparation. Calculated as Ca these weight ranges are 8-40 weight-%, 16-38 weight-% and 24-36 weight-%, respectively.

By the expression "prebiotics" it is generally meant non-digestible food ingredients that beneficially affect the host by selectively stimulating the growth and/or activity of one or a limited number of bacteria in the intestines, and thus improve host health. Suitable prebiotics to be used in the probiotic preparations of the invention include without any limitation soybean flour; psyllium, carob, gum arabic, guar gum, cassia, tamarind kernel, karaya gum, tragacanth gum, xanthan gum, gellan gum, tara gum; beta-glucan and hydrolysates thereof; oligosaccharides of oat; monosaccharides such as tagatose, and derivatives thereof; disaccharides such as lactose, lactulose, trehalose, melibiose, cellobiose, raffinose, stachyose, isomaltose, isomaltulose, and derivatives thereof; fructo-oligosaccharides, gluco-oligosaccharides, galacto-oligosaccharides, xylo-oligosaccharides, gentio-oligosaccharides, malto-oligosaccharides, isomalto-oligosaccharides, chito-oligosaccharides, manno-oligosaccharides, and derivatives thereof; poly- and oligosaccharides such as arabinogalactan, galactomannan, pectin, lignin, soybean hemicellulose, xylan, pullulan, inulin, arrow root, liquorice root, sugar beet pulp, tapioca, resistant starch of corn, barley, oat, and derivatives thereof; dextrins such as maltodextrins, cyclodextrins and derivatives thereof; processed Eucheuma seaweed, Irish moss; and any combinations thereof. Prebiotics are shown to survive in the GI tract promoting the metabolism and growth of lactic acid bacteria as well as to alter the existing intestinal microbes towards favourable microbiota. The amount of the prebiotic(s) ranges from 0.5 to 50 weight-%, preferably from 0.5 to 20 weight-%. The combination of the prebiotic substances are chosen according to their capability to enhance the survival of selected lactobacilli throughout products shelf-life and to enhance the growth when fed to dogs.

Additionally the probiotic preparation of the invention may comprise conventional excipients such as colloidal silicon dioxide, calcium silicate, magnesium silicate, magnesium trisilicate, talc, sodium aluminium silicate, potassium aluminium silicate, calcium aluminium silicate, bentonite, aluminium silicate, magnesium stearate, flavouring agents, and colouring agents, to improve preparation's shelf-life, flowing characteristics, appearance, flavour etc. Typically the excipients are present in an amount ranging from 0 to 5 weight-%, preferably from 0.9 to 1.5 weight-% of the dry weight of the preparation.

Without wishing to be bound by any theory, it is believed that the benefits of the present preparation when used for treating canine gastrointestinal disorders derive from the dog-specificity of the strains of lactic acid bacteria, the relatively high amount of each strain, and the use of more than one strain belonging to genus *Lactobacillus*. *Lactobacillus* sp. are known to be safe, and have shown to be able to colonise intestines, thus having longer wash-out period, and also to contribute to the colonisation of beneficial bacteria already present in the intestines of the subject being treated. The high Ca content produces a positive effect on the lumen stability possibly by affecting the interstices of intestinal epithelium and reducing leakage of fluids from the body into the intestines. The prebiotics used in the preparation of the invention contribute to the viability of the strains in the preparation and also to their ability to colonise the intestines after consumption. The prebiotics alter selected intestinal microbiota by fermentation and therefore ensure the effectiveness of the probiotics. The prebiotics may also act as enhancers of calcium absorption, and bind excessive liquid from stool. However, the exact mechanisms inducing the beneficial effects of the present preparation remain unknown.

The probiotic preparation of the invention may be manufactured by a process including culturing either separately or together at least two dog-specific strains of lactic acid bacteria belonging to genus *Lactobacillus* and processing the obtained culture(s), at least one prebiotic and a calcium source present in an amount of 20-99 weight-%, expressed as $CaCO_3$ of the dry weight of the final preparation, and optionally additional dog-specific strains of lactic acid bacteria, conventional excipients and carriers, into a homogenous preparation.

The strains of the lactic acid bacteria, calcium source and prebiotic(s), as well as the conventional excipients, and their amounts, are selected as disclosed above in connection with the probiotic preparation of the invention.

The dog-specific strains of lactic acid bacteria are cultured all together or preferably separately in liquid culture medium containing at least one carbon source and nitrogen source. Examples of suitable carbon sources include without limitation glucose, dextrose, and whey, alone or in combinations. Examples of suitable nitrogen sources include without limitation soybean flour, peptone, casein hydrolysate, meat extract, and yeast extract, dry yeast, non-specific protein-containing sources e.g. farmamedia, alone or in combinations. The dog-specific strains of lactic acid bacteria are cultured in the limited presence of oxygen without agitation or with gentle agitation until maximum cell density has been reached. Continuing any further will only lead to increased cell death. The pH of the cultures may range between 3.5 and 7, preferably it is between 4 and 6. The temperature may range between +25° C. and 37° C., preferably it is +30° C.±2° C. In this way, cell densities of at least $1 \times 10^9$ cfu/ml are obtained.

The cultivated cells are separated from the broth with any method including, without limitations, centrifuging, filtration or decantation. The cells separated from the fermentation broth are optionally washed by water, saline (0.9% NaCl) or with any suitable buffer. The wet cell mass obtained is dried by suitable method and preferably by lyophilisation. To enhance water adsorption there are several agents that are useful in drying while improving the stability of probiotics including, without any limitations, sucrose, maltodextrin, starch and other carbohydrates.

Several auxiliary substances may be used in production of probiotics by fermentation. There are several possible components to be added to enhance the growth of lactobacilli by fermentation and the traces are advantageous to the final composition. The possible substances include e.g. a range of antifoam agents such as oil-based agents, silicone based materials, structol and, polypropylene or polyethylene glycols, without any limitation to those.

The processing of the obtained cultures and a calcium source and at least one prebiotic into a homogenous preparation may involve any of the following in any order: lyophilising, centrifuging, filtering, drying, mixing, kneading, extruding, granulating, compressing, encapsulating, film-coating, and embedding or enclosing into control-released formulations. Optionally the strains are microencapsulated before processing with the calcium source and prebiotics, this being preferred when the end product is a high water-content formulation, such as a paste or gel.

In a preferred embodiment of the process a first amount of said at least one prebiotic is incorporated into the culture media of the dog-specific strains of lactic acid bacteria, the obtained cultures are optionally combined and washed, lyophilised and subsequently mixed with the calcium source and optionally with a second amount of said at least one prebiotic. By the expression "a first amount" it is meant any portion ranging from 0 to 100 weight-% of the total amount of the prebiotics, said first amount usually ranging from 0.001 to 30 weight-%, preferably being up to 15 weight-% of the dry weight of the preparation. By the expression "a second amount" it is meant the remaining portion of the total amount of the prebiotics not incorporated as said first amount. By incorporating a first amount of the prebiotics already into the culture media, partially fermented residues thereof may remain—depending on the selected processing steps—in the probiotic preparation thus providing easily available material facilitating the colonisation of the probiotic strains.

The process of the invention may further comprise a step of formulating the lactic acid bacteria, the calcium source and the prebiotic(s), and optionally additional dog-specific strains of lactic acid bacteria, conventional excipients and carriers, into oral formulations in the form of powders, granules, pills, tablets, capsules, lozenges, dry products for reconstitution with water or other suitable carrier, aqueous or oily solutions or suspensions, gels, pastes, emulsions or syrups, or with conventional dog food ingredients into dry food pellets, chunks, canned food, savory sauce, biscuits, chewing snacks, puppy milk replacer or fermented products. The formulating may be carried out by conventional techniques, as described for example in "Remington: The Science and Practice of Pharmacy", Lippincott, Williams and Wilkins Eds, December 2000, using suitable known binders, diluents, tabletting agents, lubricants, disintegrants, wetting agents, suspending agents, emulsifiers, non-aqueous carriers, preservatives, flavours or dyes as excipients and carriers. The preparation may also be formulated into a conventional dog food or specialty dog food products using conventional manufacturing methods and ingredients.

The preparation of the invention will be used in such doses as to provide a daily intake within the following exemplary ranges:

Each probiotic strain: $2*10^6$-$2*10^{10}$ cfu/kg/day, preferably $1*10^8$-$5*10^8$ cfu/kg/day Calcium: 40-198 mg/kg/day, preferably 80-190 mg/kg/day (expressed as calcium carbonate)

Prebiotics: 1-100 mg/kg/day, preferably 1-40 mg/kg/day.

Examples of doses of a dry powder preparation of the invention fed to a 10 kg dog without difficulty range from 0.5-4 g, a preferable dose being 2 g per 10 kg dog.

Since the lactic acid bacteria in the preparation are of canine origin, and only known prebiotics and calcium sources acceptable in food are used in the preparation, no adverse effects are anticipated. Usually the probiotic preparation of the invention is fed for periods of 5-10 days. Due to its safety, the probiotic preparation of the invention is particularly useful when treating chronic gastrointestinal disorders. In chronic disorders the probiotic preparation can be fed for substantially longer periods, such as for several months.

Preferably the probiotic preparation is in such a form that the amount of the preparation can be easily dosed for dogs based on their weight for example with a measuring spoon. The type of the formulation influences also the shelf life of the product, dry formulations being preferred due to better stability. Examples of the preferred forms include dry powders and granules.

The probiotic preparation of the invention may also be incorporated into ready-to-use canine food such as fresh dog food, dog sausages, frozen dog food, canned dog food, stews, chunks, dry pellets, kibbles, or pre-mixes. In this case the amount of the preparation in the dog food is adjusted so that one meal or part of it, or all the meals, may be replaced by the dog food comprising the probiotic preparation of the invention. The probiotic preparation of the invention may also be provided in a separate package, e.g. in a sachet, attached to the dog food package to be mixed with the dog food prior to ingestion. The probiotic preparation of the invention may also be incorporated into canine specialty products such as fermented products, puppy milk replacer, capsules, savory sauce, biscuits, chewing snacks or treats. In case of a fermented dairy product, the product may contain in addition to the preparation of the present invention water or milk, flavours, technical bacteria strains for fermenting, and other conventional ingredients of curdled milk, sour whole milk, yoghurt etc. In case of a puppy milk replacer the preparation of the invention is incorporated into conventional puppy milk replacer ingredients either as a ready-to-use product, or the preparation, provided separately e.g. in a sachet, is mixed with the puppy milk replacer just before use, or the preparation is incorporated into a dry powder puppy milk replacer pre-mix to be recovered prior use with water, milk or other suitable liquid. In case of capsules the preparation of the invention, e.g. in a form of a powder or suspension, is filled into conventional hard or soft capsules for example of gelatine. In case of dog biscuits, chewing snacks, treats or savory sauces, the preparation of the invention is incorporated to conventional biscuit, chewing snack, treat or savory sauce ingredients, e.g. by mixing or by coating, as a ready-to-use product.

The probiotic preparation of the invention is useful for preventing and treating a variety of canine gastrointestinal disorders. The probiotic preparation of the invention is particularly useful for treating small-intestine related disorders. Examples of such disorders are viral and bacterial infections, antibiotic-responsive enteropathy (ARE), and inflammatory bowel disease (IBD). In addition, probiotic *L. salivarius* has been shown to clear pathogens in the GI-tract and thus, decreasing the risk of acting as a symptomless pathogen carrier in the family. It is well known that family members, i.e. small children may receive pathogen infections from pets.

The probiotic preparation of the invention is particularly useful for treating gastrointestinal disorders not responding to other treatment. The probiotic preparation of the invention is also useful for treating gastrointestinal disorders caused by unknown or multiple sources, or having changing or complex symptoms. It can be used alone, or simultaneously with a medication, also with some antibiotics. Using the probiotic preparation of the invention simultaneously with a medication known to cause gastrointestinal problems is particularly beneficial.

Other examples of preferable application is use before and during stressful situations, such as mating season, service, gestation, delivery, lactation, weaning and neonatal maternal separation. Gestating bitches may benefit from the preparation especially through enhancement of the immune system, prevention of stress-related symptoms, and prevention of post-labour infections. New born and puppies may benefit from the preparation especially through strengthening of natural microbial interaction in the GI-tract, enhancement of the immune system, suppressing of allergies, and avoiding puppy diarrhoea when changing diet to solid food. Adult dogs may benefit from the preparation especially through curing and prevention of gastrointestinal conditions such as antibiotic associated diarrhoea, prevention of allergies, prevention of infections such as ear, skin, vaginal, and urinary infections, maintenance of oral and dental hygiene, and prevention of stress-related symptoms. Aging dogs may benefit from the preparation especially through strengthening of natural microbial interaction in the GI-tract, enhancement of the immune system and maintenance of resistance to diseases, prevention of stress-related symptoms, and prevention of infections such as ear, skin, vaginal, and urinary infections. The probiotic preparation of the invention may also be found beneficial in order to prevent gastrointestinal disorders when travelling by car, train or airplane, relocating, changing diet, visiting veterinary clinics and before/during hospitalisation due to surgical operations, and for hunting and competing dogs. The probiotic preparation of the invention maintains the healthy balance in the canine GI tract during severe training, competing, and rest periods.

Non-limiting examples of the primary and secondary disorders which may benefit from the use of the probiotic preparation of the invention include inflammatory disorders, immunodeficiency, inflammatory bowel disease, irritable bowel syndrome, cancer (particularly those of the gastrointestinal and immune systems), diseases involving diarrhoea, antibiotic associated diarrhoea, appendicitis, autoimmune disorders, multiple sclerosis, Alzheimer's disease, amyloidosis, rheumatoid arthritis, arthritis, joint mobility, diabetes mellitus, insulin resistance, bacterial, viral and fungal infections, periodontal disease, diseases of oral cavity, urogenital disease, surgical associated trauma, surgical-induced metastatic disease, sepsis, weight loss, weight gain, excessive adipose tissue accumulation, anorexia, fever control, cachexia, wound healing, ulcers, gut barrier infection, allergy, asthma, respiratory disorders, circulatory disorders, coronary heart disease, anaemia, disorders of the blood coagulation system, renal disease, disorders of the central nervous system, hepatic disease, ischaemia, nutritional disorders, osteoporosis, endocrine disorders, epidermal disorders, and furunculosis. Preferred are treatment of the gastrointestinal tract, including treatment or prevention of diarrhoea; immune system regulation, preferably the treatment or prevention of autoimmune disease and inflammation; maintaining or improving the health of the skin and/or coat system, preferably treating or preventing atopic disease of the skin; maintaining or improving the health of the nails; ameliorating or reducing the effects of aging, including mental awareness and activity levels; and preventing weight loss during and following infection.

EXAMPLES

Manufacture of the Probiotic Preparation

Selection of the Probiotic Strains

*Lactobacillus fermentum*, *Lactobacillus plantarum* and *Lactobacillus rhamnosus* were isolated from faeces of healthy canines by Beasley et al 2006, in the article referred to as LAB8 (*L. fermentum*), LABS (*L. plantarum*, previously identified as *L. salivarius*) and LAB 11 (*L. rhamnosus*). Here, these strains are referred to by their deposit numbers NCIMB 41636, NCIMB 41638 and NCIM 41640, respectively. These bacteria have been demonstrated to survive low pH (pH 1) and can be cultured after collection from canine jejunum (Beasley et al 2006; Manninen et al, 2006). The strains alter the pre-existing intestinal microbiota facilitating the survival of the host specific lactic acid bacteria already present. Intestinal modification in conjuction with antimicrobial activity enhance the probiotic nature of these strains. These strains have also been shown to tolerate common oral antibiotics given to dogs. Due to this feature the strains can be given simultaneously with antibiotics to reduce antibiotic-induced diarrhoea, such as cephalosporins.

Culture Conditions

*Lactobacillus fermentum* NCIMB 41636, *Lactobacillus plantarum* NCIMB 41638 and *Lactobacillus rhamnosus* NCIMB 41640 were inoculated separately from the freshly prepared agar plate culture or from a freezed culture stock in 20% glycerol to the MRS (De Man, Rogosa & Sharpe)-medium (content: peptone (Bacto Peptone, Becton Dickinson) 10 g/l, meal extract (Organotechnie) 8 g/l, yeast extract (DSM Food Specialties) 4 g/l, dextrose 20 g/l, $K_2HPO_4 \times 3 H_2O$ 2.6 g/l, $CH_3COONa \times 3H_2O$ 5 g/l, triammonium citrate 2 g/l, $MgSO_4 \times 7$ $H_2O$ 0.2 g/l and $MnSO_4 \times 1$ $H_2O$ 0.04 g/l and the cultivation was allowed to continue for 16-18 h at 30° C. without shaking. The culture broth obtained was used to seed a 500 L of fermentation medium with 1% transferring rate. The production medium was as follows:

| Component | Supplier | g/L |
| --- | --- | --- |
| Glucose (Dextrose) | | 24 |
| Soy Flour 7B | ADM prod code 063130 | 30 |
| Yeast extract | R1012-1592F | 10 |
| $K_2HPO_4$ | A687601604 | 2.5 |
| Sodium acetate trihydrate | Riedel de Haen 32318 | 7.5 |
| $MnSO_4 \times 1H_2O$ | MP Biomedicals 194702 | 0.1 |

As antifoam agent silicon based agent was used. The fermentation was carried out at 30° C. without aeration and with minimal agitation for one day. After reaching the OD600 value of 10, corresponding to the $6.0*10^9$; $4.0*10^9$; $4.0*10^9$ cfu/ml for *Lactobacillus fermentum* NCIMB 41636, *Lactobacillus plantarum* NCIMB 41638 and *Lactobacillus rhamnosus* NCIMB 41640, respectively, the cells were harvested by a separator (Seital SE 12 X). The wet cell masses of each Lactobacillus strain obtained from the 500 L fermentation culture broths were washed with water, supplemented with maltodextrin and dried by lyophilisation (Hetosicc Freeze dryer CD 15-1) for 3 days. Considering the value of cfu/mg, the yields after lyophilization for *Lactobacillus fermentum* NCIMB 41636, *Lactobacillus plantarum* NCIMB 41638 and NCIMB 41640 were 90.1%, 47.1% and 45.6%, respectively. The residues of fermentation broth after washing contain minor quantities of soybean flour, e.g. 1-5 g/l and no other residues were found to be fully soluble component in the cultivation broth.

The following components were added to the lyophilized probiotics: psyllium 80-100 mesh to enhance prebiotic properties of the final product and to improve stability of the probiotic product in an amount of 1.5 weight-%, and $CaCO_3$ in an amount of 87.5 weight-%. The stability of the product was studied and observed overall good. The titres of viable Lactobacillus cells remained almost stable, $9.7 \times 10^8$ cfu/g.

Preliminary Test on Dogs Suffering from Diarrhoea

A probiotic preparation of the invention (powdery preparation containing $3 \times 10^8$-$6.7 \times^8$ cfu/g each of Lactobacillus strains *L. fermentum* NCIMB 41636, *L. plantarum* NCIMB 41638 and *L. rhamnosus* NCIMB 41640; 87.5 weight-% of $CaCO_3$; 5.0 weight-% of psyllium; 5.0 weight-% of soybean flour; and 1 weight-% of silica oxide) was fed to dogs suffering from gastrointestinal disorders, such as diarrhoea, allergy and weight problems as a dose of 1 g preparation per 10 kg dog for 3-7 days. Lactating bitches (n=2, age 4 years) and their weaning pups (n=7 age 1 week, n=6 age 4 weeks, n=3 age 5 weeks) suffered from post delivery diarrhoea. For adult dogs the preparation was fed mixed into dog food. Newborn puppies were let to lick the preparation from fingertip dipped into the preparation. One gram of preparation was daily added to soaked dry food pellets of pups aged 4 weeks and 5 weeks. In all cases the diarrhoea ceased within 2-3 days after starting the treatment and did not recur in pups aged 1 week and 5 weeks after the treatment had ended. Pups aged 4 week were noticed to have loose stole occasionally after one week without preparation.

Preliminary Test on Dog Suffering from Severe Food Allergy

The same probiotic preparation of the invention as in previous example was tested on a dach hund with severe food allergy (n=1, age 1 years) using dose of 1 g preparation per 10 kg dog for 7 days with good results: individual tolerated preparation and all food during 7 days without any symptoms.

Preliminary Test on Dog Suffering from Chronic Intermittent Diarrhoea

The same probiotic preparation of the invention as in previous examples was tested on a male rottweiler with chronic intermittent diarrhoea (n=1, age 7 years) using dose of 1 g preparation per 10 kg dog (i.e. 4 teaspoonfuls) for 7 days with good results: diarrhoea ceased for 3 weeks.

The invention claimed is:

1. A probiotic preparation for treating and/or reducing the risk of developing canine gastrointestinal disorders containing effective amounts of:
    at least two lactic acid producing bacteria strains isolated from canine faeces, canine intestines or intestinal fluids, belonging to the genus *Lactobacillus*, said bacteria strains being selected from the group consisting of *Lactobacillus fermentum* NCIMB 41636, *Lactobacillus plantarum* NCIMB 41638, and *Lactobacillus rhamnosus* NCIMB 41640,
    a calcium source in an amount of 20-99 weight-% expressed as $CaCO_3$ of the dry weight of the preparation, and
    at least one prebiotic, and
    optionally additional lactic acid producing bacteria strains isolated from canine faeces, canine intestines or intestinal fluids, belonging to genus *Lactobacillus*, genus *Pediococcus* or genus *Weissella*, excipients and carriers.

2. The probiotic preparation according to claim 1, wherein the amount of each of the lactic acid producing bacteria strains ranges between $1*10^7$-$1*10^{10}$ cfu/g and the amount of the prebiotic(s) ranges between 0.5-50 weight-% of the dry weight of the preparation.

3. The probiotic preparation according to claim 1, wherein the amount of each of lactic acid producing bacteria strains ranges between $5*10^8$-$2.5*10^9$ cfu/g, the amount of the prebiotic(s) ranges between 0.5-20 weight-%, and the amount of the calcium source ranges between 40-95 weight-% expressed as $CaCO_3$ of the dry weight of the preparation.

4. The probiotic preparation according to claim 1, wherein said lactic acid producing bacteria strains belonging to the genus *Lactobacillus* are a combination of *Lactobacillus fermentum* NCIMB 41636 and *Lactobacillus plantarum* NCIMB 41638.

5. The probiotic preparation according to claim 1, wherein said lactic acid producing bacteria strains belonging to the genus *Lactobacillus* are a combination of *Lactobacillus fermentum* NCIMB 41636, *Lactobacillus plantarum* NCIMB 41638 and *Lactobacillus rhamnosus* NCIMB 41640.

6. The probiotic preparation according to claim 1, wherein the calcium source is selected from the group consisting of calcium carbonate, calcium ascorbate, calcium alginate, calcium stearoyl-2-lactylate, calcium sorbate, calcium formiate, calcium acetate, calcium propionate, calcium lactate, calcium citrate, calcium stearates, synthetic calcium silicate, calcium tetrahydrogen-diorthophosphate, calcium hydrogen-orthophosphate, calcium hydroxide, calcium oxide, dicalcium diphosphate, calcium gluconate, calcium sulphite, calcium hydrogensulphite, calcium aluminium silicate, calcium digluconate, calcium guanylate, calcium inosinate, calcium-5'-ribonucleotides, calcium malate, calcium tartrate, calcium dinatrium EDTA, mono and dicalciumdiphosphate, (sodium) calciumpolyphosphate, calcium chloride, calcium ferrocyanide, calcium orthophosphate, and combinations thereof.

7. The probiotic preparation according to claim 1, wherein said at least one prebiotic is selected from the group consisting of soybean flour; psyllium, carob, gum arabic, guar gum, cassia, tamarind kernel, karaya gum, tragacanth gum, xanthan gum, gellan gum, tara gum; beta-glucan and hydrolysates thereof; oligosaccharides of oat;
    monosaccharides such as tagatose, and derivatives thereof; disaccharides such as lactose, lactulose, trehalose, melibiose, cellobiose, raffinose, stachyose, isomaltose, isomaltulose, and derivatives thereof; fructo-oligosaccharides, gluco-oligosaccharides, galacto-oligosaccharides, xylo-oligosaccharides, gentio-oligosaccharides, malto-oligosaccharides, isomalto-oligosaccharides, chito-oligosaccharides, manno-oligosaccharides, and derivatives thereof; poly- and oligosaccharides such as arabinogalactan, galactomannan, pectin, lignin, soybean hemicellulose, xylan, pullulan, inulin, arrow root, liquorice root, sugar beet pulp, tapioca, resistant starch of corn, barley, oat, and derivatives thereof dextrins such as maltodextrins, cyclodextrins and derivatives thereof; processed Eucheuma seaweed, Irish moss, and any combinations thereof.

8. The probiotic preparation according to claim 1, wherein the probiotic preparation is in the form of dry powders, granules, pills, tablets, capsules, lozenges, dry products for reconstitution with water or other suitable carrier, aqueous or oily solutions or suspensions, gels, pastes, emulsions or syrups.

9. The probiotic preparation according to claim 8, wherein the probiotic preparation is in the form of a dry powder.

10. A dog food product for treating and/or reducing the risk of developing canine gastrointestinal disorders containing the probiotic preparation according to claim 1, wherein the probiotic preparation is formulated into fresh food, sausages, frozen food, dry food pellets, kibbles, chunks, canned food, stews, pre-mixes, savoury sauce, biscuits, chewing snacks, treats, or puppy milk replacer.

11. A process for manufacturing the probiotic preparation according to claim 1, comprising:
    culturing either separately or together at least two lactic acid producing bacteria strains isolated from canine faeces, canine intestines or intestinal fluids, wherein the at least two lactic acid producing bacterial strains in a culture media are selected from the group consisting of *Lactobacillus fermentum* NCIMB 41636, *Lactobacillus plantarum* NCIMB 41638, and *Lactobacillus rhamnosus* NCIMB 41640; and
    combining the obtained culture(s), the at least one prebiotic, the calcium source, and optionally one or more additional lactic acid producing bacteria strains isolated from canine faeces, canine intestines or intestinal fluids, belonging to the genus *Lactobacillus*, the genus *Pedio-*

*coccus* and/or the genus *Weissella*, excipients and carriers, into a homogenous preparation to obtain said probiotic preparation, wherein the calcium source is CaC03 and is present in the probiotic preparation in an amount of 20-99 weight-%, on a dry weight basis.

12. The process according to claim 11, wherein at least one prebiotic is incorporated into the culture media and wherein the obtained cultures are optionally combined and washed, lyophilized and subsequently mixed with the calcium source and optionally with a second amount of a prebiotic.

13. The process according to claim 11, further comprising formulating the probiotic preparation into an oral formulation selected from the group consisting of powders, granules, pills, tablets, capsules, lozenges, dry products for reconstitution with water or other suitable carrier, aqueous or oily solutions or suspensions, gels, pastes, emulsions or syrups, dog food, sausages, frozen food, dry food pellets, kibbles, chunks, canned food, stews, pre-mixes, savoury sauce, biscuits, chewing snacks, treats, and puppy milk replacers.

14. A method of treating a canine gastrointestinal disorder, said method comprising administering an effective amount of the probiotic preparation according to claim 1 to a dog in need thereof.

* * * * *